(12) United States Patent
McKenna

(10) Patent No.: US 9,078,610 B2
(45) Date of Patent: Jul. 14, 2015

(54) MOTION ENERGY HARVESTING WITH WIRELESS SENSORS

(75) Inventor: Edward McKenna, Boulder, CO (US)

(73) Assignee: COVIDIEN LP, Mansfield, MA (US)

(*) Notice: Subject to any disclaimer, the term of this patent is extended or adjusted under 35 U.S.C. 154(b) by 719 days.

(21) Appl. No.: 12/709,696

(22) Filed: Feb. 22, 2010

(65) Prior Publication Data

US 2011/0208010 A1    Aug. 25, 2011

(51) Int. Cl.
*A61B 5/00* (2006.01)
*F03G 7/08* (2006.01)
*A61B 5/1455* (2006.01)
*F03G 5/06* (2006.01)
*A61B 5/024* (2006.01)

(52) U.S. Cl.
CPC .......... *A61B 5/14552* (2013.01); *A61B 5/14551* (2013.01); *A61B 5/6826* (2013.01); *A61B 5/6838* (2013.01); *F03G 5/06* (2013.01); *A61B 5/02438* (2013.01); *A61B 2560/0214* (2013.01)

(58) Field of Classification Search
CPC .. A61B 5/14552; A61B 5/14551; F03G 5/06; F03G 5/08
USPC ......................................................... 600/323
See application file for complete search history.

(56) References Cited

U.S. PATENT DOCUMENTS

| | | | |
|---|---|---|---|
| 3,721,813 A | 3/1973 | Condon et al. | |
| 4,332,006 A * | 5/1982 | Choe | 362/193 |
| 4,971,062 A | 11/1990 | Hasebe et al. | |
| 4,974,591 A | 12/1990 | Awazu et al. | |
| 5,001,685 A | 3/1991 | Hayakawa | |
| 5,028,787 A | 7/1991 | Rosenthal et al. | |
| 5,035,243 A | 7/1991 | Muz | |
| 5,065,749 A | 11/1991 | Hasebe et al. | |
| 5,084,327 A | 1/1992 | Stengel | |
| 5,094,240 A | 3/1992 | Muz | |
| 5,275,159 A | 1/1994 | Griebel | |
| 5,348,003 A | 9/1994 | Caro | |

(Continued)

FOREIGN PATENT DOCUMENTS

| | | |
|---|---|---|
| DE | 3516338 | 11/1986 |
| DE | 3703458 | 8/1988 |

(Continued)

OTHER PUBLICATIONS

Crilly, Paul B., et al.; "An Integrated Pulse Oximeter System for Telemedicine Applications," *IEEE Instrumentation and Measurement Technology Conference*, May 19-21, 1997; pp. 102-104; Ottawa, Canada.

(Continued)

*Primary Examiner* — Sean Dougherty
*Assistant Examiner* — Michael C Stout
(74) *Attorney, Agent, or Firm* — Fletcher Yoder PC

(57) ABSTRACT

A system and method for generating power when one or more motion sensitive structures are moved. The system may include one or more sensing components which, acting alone or in combination, are capable of generating data related to one or more physiological parameters. The system may also include wireless communication circuitry capable of wirelessly transmitting the data related to the one or more physiological parameters. Furthermore, at least one of the one or more sensing components or the wireless communication circuitry may be at least partially powered, directly or indirectly, by the one or more motion sensitive structures.

22 Claims, 6 Drawing Sheets

(56) References Cited

U.S. PATENT DOCUMENTS

| | | | |
|---|---|---|---|
| 5,429,129 A | 7/1995 | Lovejoy et al. | |
| 5,465,714 A | 11/1995 | Scheuing | |
| 5,474,065 A | 12/1995 | Meathrel et al. | |
| 5,483,646 A | 1/1996 | Uchikoga | |
| 5,511,546 A | 4/1996 | Hon | |
| 5,578,877 A | 11/1996 | Tiemann | |
| 5,619,992 A | 4/1997 | Guthrie et al. | |
| 5,666,952 A | 9/1997 | Fuse et al. | |
| D393,830 S | 4/1998 | Tobler et al. | |
| 5,779,631 A | 7/1998 | Chance | |
| 5,835,996 A * | 11/1998 | Hashimoto et al. | 323/364 |
| 5,871,442 A | 2/1999 | Madarasz et al. | |
| 6,006,120 A | 12/1999 | Levin | |
| 6,081,742 A | 6/2000 | Amano et al. | |
| 6,139,488 A * | 10/2000 | Ball | 600/25 |
| 6,144,444 A | 11/2000 | Haworth et al. | |
| 6,261,236 B1 | 7/2001 | Grimblatov | |
| 6,285,895 B1 | 9/2001 | Ristolainen et al. | |
| 6,353,750 B1 | 3/2002 | Kimura et al. | |
| 6,375,609 B1 * | 4/2002 | Hastings et al. | 600/104 |
| 6,419,671 B1 | 7/2002 | Lemberg | |
| 6,461,305 B1 | 10/2002 | Schnall | |
| 6,483,781 B2 * | 11/2002 | Igarashi et al. | 368/66 |
| 6,512,937 B2 | 1/2003 | Blank et al. | |
| 6,564,088 B1 | 5/2003 | Soller et al. | |
| 6,589,172 B2 | 7/2003 | Williams et al. | |
| 6,591,122 B2 | 7/2003 | Schmitt | |
| 6,750,971 B2 * | 6/2004 | Overbeck et al. | 356/405 |
| 6,791,689 B1 | 9/2004 | Weckström | |
| 6,793,654 B2 | 9/2004 | Lemberg | |
| 6,916,289 B2 | 7/2005 | Schnall | |
| 6,971,580 B2 | 12/2005 | Zhu et al. | |
| 6,992,751 B2 | 1/2006 | Okita et al. | |
| 7,102,964 B2 * | 9/2006 | Fujisawa | 368/66 |
| 7,154,398 B2 * | 12/2006 | Chen et al. | 340/573.1 |
| 7,154,816 B2 * | 12/2006 | Igarashi et al. | 368/66 |
| 7,198,778 B2 | 4/2007 | Mannheimer et al. | |
| 7,204,041 B1 * | 4/2007 | Bailey et al. | 36/29 |
| 7,236,811 B2 | 6/2007 | Schmitt | |
| 7,236,881 B2 | 6/2007 | Liu et al. | |
| 7,313,427 B2 | 12/2007 | Benni | |
| 7,382,263 B2 * | 6/2008 | Danowski et al. | 340/572.1 |
| 7,469,158 B2 | 12/2008 | Cutler et al. | |
| 7,572,229 B2 | 8/2009 | Yeo et al. | |
| 7,574,244 B2 | 8/2009 | Eghbal et al. | |
| 7,878,991 B2 * | 2/2011 | Babaev | 601/2 |
| 8,174,371 B2 * | 5/2012 | Schwieger | 340/407.1 |
| 8,406,893 B2 * | 3/2013 | Krause et al. | 607/61 |
| 2001/0043512 A1 * | 11/2001 | Igarashi et al. | 368/204 |
| 2002/0103425 A1 * | 8/2002 | Mault | 600/373 |
| 2002/0109808 A1 * | 8/2002 | Sekiguchi et al. | 349/96 |
| 2003/0065269 A1 * | 4/2003 | Vetter et al. | 600/503 |
| 2003/0069486 A1 * | 4/2003 | Sueppel et al. | 600/322 |
| 2003/0184165 A1 * | 10/2003 | Chiu | 310/47 |
| 2004/0098009 A1 | 5/2004 | Boecker et al. | |
| 2004/0190383 A1 * | 9/2004 | Marcucelli et al. | 368/278 |
| 2004/0230106 A1 * | 11/2004 | Schmitt et al. | 600/310 |
| 2004/0264304 A1 * | 12/2004 | Furukawa et al. | 368/223 |
| 2005/0075550 A1 | 4/2005 | Lindekugel | |
| 2005/0096561 A1 * | 5/2005 | Conn et al. | 600/559 |
| 2005/0113656 A1 | 5/2005 | Chance | |
| 2005/0177034 A1 | 8/2005 | Beaumont | |
| 2005/0185513 A1 * | 8/2005 | Tamura et al. | 368/28 |
| 2005/0197548 A1 | 9/2005 | Dietiker | |
| 2005/0228298 A1 * | 10/2005 | Banet et al. | 600/485 |
| 2005/0228301 A1 * | 10/2005 | Banet et al. | 600/485 |
| 2005/0234317 A1 | 10/2005 | Kiani | |
| 2005/0245839 A1 * | 11/2005 | Stivoric et al. | 600/549 |
| 2006/0058594 A1 | 3/2006 | Ishizuka et al. | |
| 2006/0069320 A1 * | 3/2006 | Wolff et al. | 600/509 |
| 2006/0106323 A1 * | 5/2006 | Bischoff et al. | 600/515 |
| 2006/0220881 A1 * | 10/2006 | Al-Ali et al. | 340/573.1 |
| 2006/0247501 A1 | 11/2006 | Ali | |
| 2006/0250043 A1 * | 11/2006 | Chung | 310/216 |
| 2006/0291259 A1 * | 12/2006 | Densham et al. | 363/63 |
| 2007/0038155 A1 * | 2/2007 | Kelly et al. | 600/595 |
| 2007/0043281 A1 * | 2/2007 | Fine | 600/335 |
| 2007/0049842 A1 | 3/2007 | Hill et al. | |
| 2007/0060786 A1 * | 3/2007 | Gura et al. | 600/16 |
| 2007/0073121 A1 | 3/2007 | Hoarau et al. | |
| 2007/0100222 A1 * | 5/2007 | Mastrototaro et al. | 600/365 |
| 2007/0102928 A1 * | 5/2007 | Yang | 290/1 C |
| 2007/0123756 A1 * | 5/2007 | Kitajima et al. | 600/300 |
| 2007/0167693 A1 * | 7/2007 | Scholler et al. | 600/301 |
| 2007/0167850 A1 * | 7/2007 | Russell et al. | 600/513 |
| 2007/0213624 A1 * | 9/2007 | Reisfeld et al. | 600/504 |
| 2007/0219430 A1 * | 9/2007 | Moore | 600/300 |
| 2007/0232887 A1 * | 10/2007 | Bettesh et al. | 600/407 |
| 2007/0276270 A1 * | 11/2007 | Tran | 600/508 |
| 2008/0001735 A1 * | 1/2008 | Tran | 340/539.22 |
| 2008/0004904 A1 * | 1/2008 | Tran | 705/2 |
| 2008/0053456 A1 * | 3/2008 | Brown et al. | 128/207.16 |
| 2008/0081002 A1 * | 4/2008 | Petruno et al. | 422/82.05 |
| 2008/0146892 A1 * | 6/2008 | LeBoeuf et al. | 600/300 |
| 2008/0167691 A1 * | 7/2008 | Weintraub | 607/5 |
| 2008/0221418 A1 * | 9/2008 | Al-Ali et al. | 600/324 |
| 2008/0275327 A1 * | 11/2008 | Faarbaek et al. | 600/382 |
| 2008/0294019 A1 * | 11/2008 | Tran | 600/301 |
| 2009/0076350 A1 * | 3/2009 | Bly et al. | 600/301 |
| 2009/0076405 A1 * | 3/2009 | Amurthur et al. | 600/529 |
| 2009/0171404 A1 * | 7/2009 | Irani et al. | 607/2 |
| 2009/0247850 A1 * | 10/2009 | Porges | 600/323 |
| 2009/0318779 A1 * | 12/2009 | Tran | 600/301 |
| 2010/0114216 A1 * | 5/2010 | Krause et al. | 607/5 |
| 2010/0179389 A1 * | 7/2010 | Moroney et al. | 600/301 |
| 2010/0191072 A1 * | 7/2010 | Matsumori et al. | 600/301 |
| 2010/0277119 A1 * | 11/2010 | Montague et al. | 320/107 |
| 2010/0317978 A1 * | 12/2010 | Maile et al. | 600/488 |
| 2010/0324403 A1 * | 12/2010 | Brister et al. | 600/365 |
| 2011/0125063 A1 * | 5/2011 | Shalon et al. | 600/590 |
| 2011/0145162 A1 * | 6/2011 | Vock et al. | 705/333 |
| 2011/0187207 A1 * | 8/2011 | Arnold et al. | 310/11 |
| 2011/0208010 A1 * | 8/2011 | McKenna | 600/300 |
| 2012/0029375 A1 * | 2/2012 | Lane et al. | 600/534 |
| 2012/0179015 A1 * | 7/2012 | Mann et al. | 600/365 |
| 2012/0179067 A1 * | 7/2012 | Wekell | 600/587 |

FOREIGN PATENT DOCUMENTS

| | | | |
|---|---|---|---|
| EP | 0127947 | 12/1984 | |
| EP | 0531631 | 3/1993 | |
| JP | 5049625 | 3/1993 | |
| JP | 6014906 | 1/1994 | |
| JP | 6269430 | 9/1994 | |
| JP | 7236625 | 9/1995 | |
| JP | 2000237170 | 9/2000 | |
| JP | 2004159810 | 6/2004 | |
| JP | 2004329406 | 11/2004 | |
| JP | 2004337605 | 12/2004 | |
| JP | 2004351107 | 12/2004 | |
| WO | WO8909566 | 10/1989 | |
| WO | WO9111137 | 8/1991 | |
| WO | WO9947039 | 9/1999 | |
| WO | WO2005010568 | 2/2005 | |
| WO | WO 2007100959 A2 * | 9/2007 | A61B 5/00 |
| WO | WO2007141121 | 12/2007 | |

OTHER PUBLICATIONS

Warren, Steve, et al.; "Wearable Sensors and Component-Based Design for Home Health Care," *Proceedings of the Second Joint EMBS/BMES Conference*, Oct. 23-26, 2002; pp. 1871-1872; Houston, Texas.

Lebak, J.W., et al.; "Implementation of a Standards-Based Pulse Oximeter on a Wearable, Embedded Platform," *Proceeding of the 25th Annual International Conference of the IEEE EMBS*, Sep. 17-21, 2003; pp. 3196-3198; Cancun, Mexico.

Nagl, L., et al.; "Wearable Sensor System for Wireless State-of-Health Determination in Cattle," *Proceeding of the 25th Annual International Conference of the IEEE EMBS*, Sep. 17-21, 2003; pp. 3012-3015; Cancun, Mexico.

(56) References Cited

OTHER PUBLICATIONS

Pujary, C., et al.; "Photodetector Size Considerations in the Design of a Noninvasive Reflectance Pulse Oximeter for Telemedicine Applications," *IEEE*, 2003, pp. 148-149.

Wendelken, Suzanne, et al.; "The Feasibility of Using a Forehead Reflectance Pulse Oximeter for Automated Remote Triage," *IEEE*, 2004, pp. 180-181.

Qin et al.; "Microfibre-nonowire hybrid structure for energy scavenging"; Nature; vol. 451; pp. 809-814; Feb. 14, 2008; Nature Publishing Group.

Mitcheson et al.; "Energy Harvesting from Human and Machine Motion for Wirless Electronic Devices"; IEEE; Sep. 2008; vol. 96, No. 9; pp. 1457-1486.

Yang et al; "Coverting Biomechanical Energy into Electricity by a Muscle-Movement-Driven Nanogenerator"; American Chemical Society, 2009; pp. 1201-1205; vol. 9, No. 3; Nano Lett., ACS Publications; Washington, DC, US.

Park; "Overview of Energy Harvesting Systems (for low-power electonics)"; The First Engineering Institute Workshop; Energy Harvesting; Jun. 28, 2005; slides 1-30; Los Alamos National Laboratory.

* cited by examiner

MOTION ENERGY HARVESTING WITH WIRELESS SENSORS

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Wireless sensors have been developed for use in measuring physiological parameters of a patient. Powering of these devices may present a challenge as there may be no wires connected to the sensor available to provide power to the sensors. While internal power sources such as batteries may be utilized, problems may exist in which the internal power source is drained, yielding an undesirable operational lifetime. Accordingly, alternate powering methods may be useful.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to a system and method for converting movement into power for powering electronic devices. The system may include one or more motion sensitive structures that, when moved, may generate electromagnetic charging signals. The system may further include one or more elements that may receive the generated electromagnetic charging signals and may utilize the electromagnetic charging signals to charge a power source, such as a rechargeable battery, of a device. Additionally and/or alternatively, the electromagnetic charging signals may be utilized to power the device directly. The device may include, but is not limited to, pulse oximetry sensors, pulse oximetry monitors, portable pulse oximeters, and/or medical implants. That is, the system may include a device with one or more sensing components which, acting alone or in combination, are capable of generating data related to one or more physiological parameters. The system may also include wireless communication circuitry capable of wirelessly transmitting the data related to the one or more physiological parameters. In one embodiment, at least one of the one or more sensing components or the wireless communication circuitry of the device may be at least partially powered, directly or indirectly, by energy harvested through movement by one or more of the motion sensitive structures.

Figure 1:
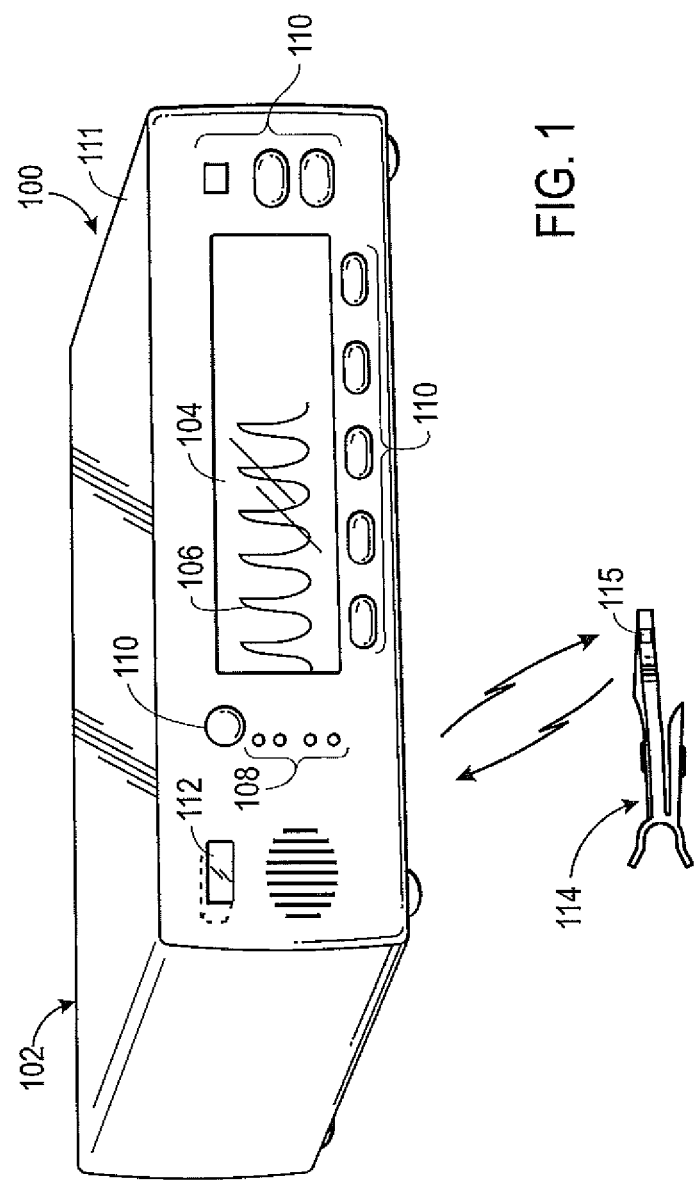
FIG. 1 illustrates a perspective view of a wireless power system including an electronic device, such as a pulse oximeter, in accordance with an embodiment.

Turning to FIG. 1, a perspective view of a medical device is illustrated in accordance with an embodiment. The medical device may be a pulse oximeter 100. The pulse oximeter 100 may include a monitor 102, such as those available from Nellcor Puritan Bennett LLC. The monitor 102 may be configured to display calculated parameters on a display 104. As illustrated in FIG. 1, the display 104 may be integrated into the monitor 102. However, the monitor 102 may be configured to provide data via a port to a display (not shown) that is not integrated with the monitor 102. The display 104 may be configured to display computed physiological data including, for example, an oxygen saturation percentage, a pulse rate, and/or a plethysmographic waveform 106. As is known in the art, the oxygen saturation percentage may be a functional arterial hemoglobin oxygen saturation measurement in units of percentage $SpO_2$, while the pulse rate may indicate a patient's pulse rate in beats per minute. The monitor 102 may also display information related to alarms, monitor settings, and/or signal quality via indicator lights 108.

To facilitate user input, the monitor 102 may include a plurality of control inputs 110. The control inputs 110 may include fixed function keys, programmable function keys, and soft keys. Specifically, the control inputs 110 may correspond to soft key icons in the display 104. Pressing control inputs 110 associated with, or adjacent to, an icon in the display may select a corresponding option. The monitor 102 may also include a casing 111. The casing 111 may aid in the protection of the internal elements of the monitor 102 from damage.

The monitor 102 may further include a transceiver 112. The transceiver 112 may allow for wireless operation signals to be transmitted to and received from an external sensor 114. In this manner, the monitor 102 and the sensor 114 may communicate wirelessly. The sensor 114 may be of a disposable or a non-disposable type. Furthermore, the sensor 114 may obtain readings from a patient that can be used by the monitor 102 to calculate certain physiological characteristics such as the blood-oxygen saturation of hemoglobin in arterial blood, the volume of individual blood pulsations supplying the tissue, and/or the rate of blood pulsations corresponding to each heartbeat of a patient. As will be discussed in greater detail below, the sensor 114 may include a charging device 115, respectively, for harnessing of energy for use by the sensor 114.

Figure 2:
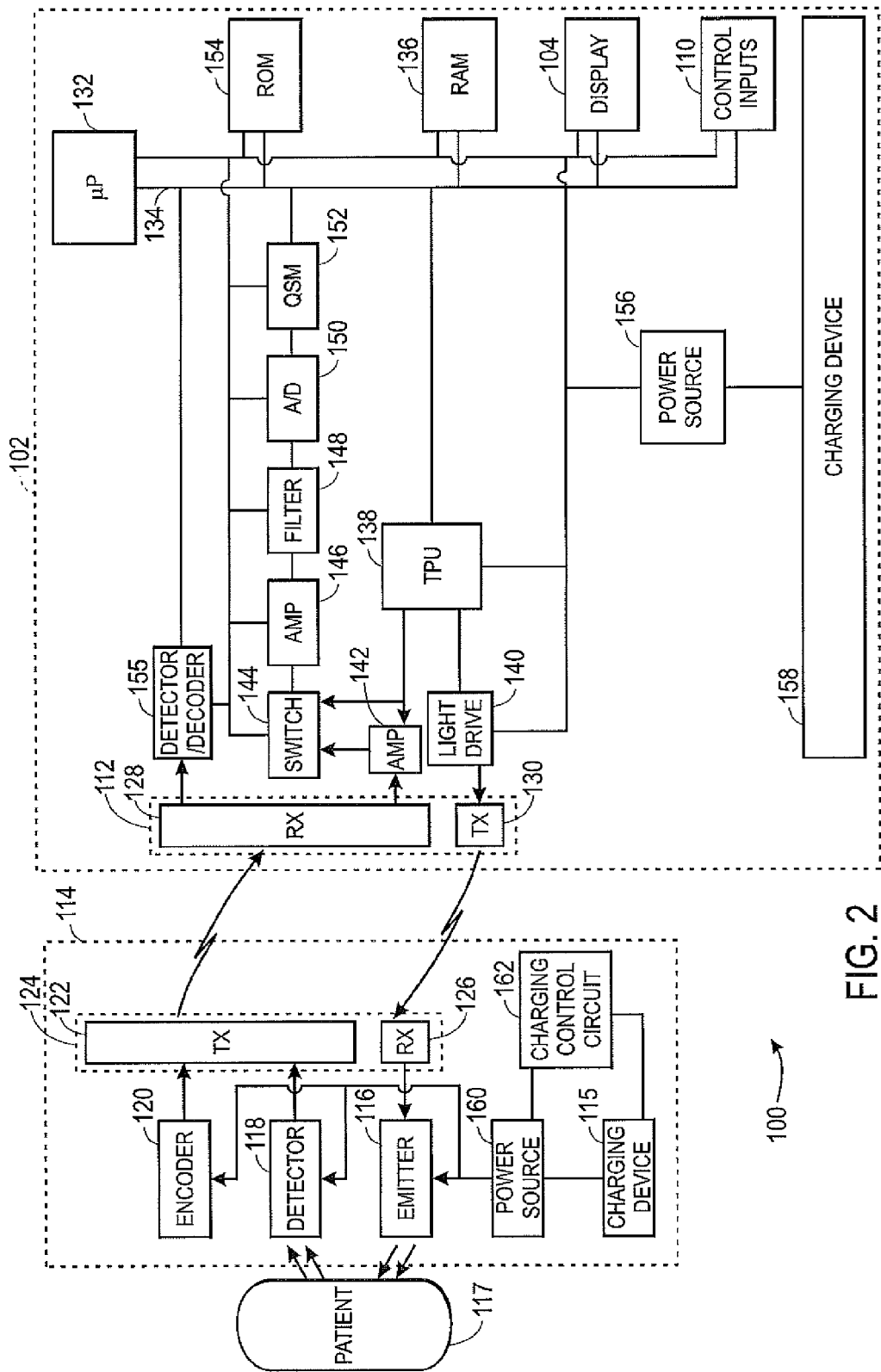
FIG. 2 illustrates a simplified block diagram of the pulse oximeter in FIG. 1, according to an embodiment.

Turning to FIG. 2, a simplified block diagram of the pulse oximeter 100 is illustrated in accordance with an embodiment. Specifically, certain components of the sensor 114 and the monitor 102 are illustrated in FIG. 2. As previously noted, the sensor 114 may include a charging device 115. The sensor 114 may also include an emitter 116, a detector 118, and an encoder 120. It should be noted that the emitter 116 may be capable of emitting at least two wavelengths of light, e.g., RED and infrared (IR) light, into the tissue of a patient 117 to calculate the patient's 117 physiological characteristics, where the RED wavelength may be between about 600 nanometers (nm) and about 700 nm, and the IR wavelength may be between about 800 nm and about 1000 nm. Alternative light sources may be used in other embodiments. For example, a single wide-spectrum light source may be used, and the detector 118 may be capable of detecting certain wavelengths of light. In another example, the detector 118 may detect a wide spectrum of wavelengths of light, and the monitor 102 may process only those wavelengths which are of interest for use in measuring, for example, water fractions, hematocrit, or other physiologic parameters of the patient 117. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

Additionally the sensor 114 may include an encoder 120, which may contain information about the sensor 114, such as what type of sensor it is (e.g., whether the sensor is intended for placement on a forehead or digit) and the wavelengths of light emitted by the emitter 116. This information may allow the monitor 102 to select appropriate algorithms and/or calibration coefficients for calculating the patient's 117 physiological characteristics. Additionally, the encoder 120 may include information relating to the proper charging of the sensor 112. The encoder 120 may, for instance, be a memory on which one or more of the following information may be stored for communication to the monitor 102; the type of the sensor 114; the wavelengths of light emitted by the emitter 116; the proper calibration coefficients and/or algorithms to be used for calculating the patient's 117 physiological characteristics; and/or information regarding a charging device for the sensor 114. The sensor 114 may be any suitable physiological sensor, such as those available from Nellcor Puritan Bennett LLC.

Signals from the detector 118 and the encoder 120 (if utilized) may be transmitted to the monitor 102 via a transmitter 122 that may be located in a transceiver 124. The transceiver 124 may also include a receiver 126 that may be used to receive signals form the monitor 102. As may be seen, the receiver 126 may transmit received signals to the emitter 116 for transmission to a patient 117. The transmitter 122 may receive signals from both the detector 118 and the encoder 120 for transmission to the monitor 102. As previously described, the signals used in conjunction with the emitter 116 and the detector 118 may be utilized for the monitoring of physiologic parameters of the patient 117 while the signals from the encoder may contain information about the sensor 114 to allow the monitor 102 to select appropriate algorithms and/or calibration coefficients for calculating the patient's 117 physiological characteristics.

As previously discussed, the monitor 102 may include a transceiver 112. The transceiver 112 may include a receiver 128 and a transmitter 130. The receiver 128 may receive transmitted signals from the transmitter 122 of the sensor 114 while the transmitter 130 of the monitor 102 may operate to transmit signals to the receiver 126 of the sensor 114. In this manner, the sensor 114 may wirelessly communicate with the monitor 102 (i.e., the sensor 114 may be a wireless sensor 114). The monitor 102 may further include one or more processors 132 coupled to an internal bus 134. Also connected to the bus may be a RAM memory 136 and the display 104. A time processing unit (TPU) 138 may provide timing control signals to light drive circuitry 140, which controls (e.g., via the transmitter 130), when the emitter 116 is activated, and if multiple light sources are used, the multiplexed timing for the different light sources. TPU 138 may also control the gating-in of signals from detector 118 through an amplifier 142 and a switching circuit 134. The amplifier 142 may amplify, for example, the signals from the detector 118 received at the receiver 128. The TPU 138 may control the gating-in of signals from detector 118 through an amplifier 142 to insure that the signals are sampled at the proper time, which may depend at least in part upon which of multiple light sources is activated, if multiple light sources are used. The received signal from the detector 118 may be passed through an (optional) amplifier 146, a low pass filter 148, and an analog-to-digital converter 150 for amplifying, filtering, and digitizing the electrical signals the from the sensor 114. The digital data may then be stored in a queued serial module (QSM) 152, for later downloading to RAM 136 as QSM 152 fills up. In an embodiment, there may be multiple parallel paths of separate amplifier, filter, and A/D converters for multiple light wavelengths or spectra received.

In an embodiment, based at least in part upon the received signals corresponding to the light received by detector 118, processor 122 may calculate the oxygen saturation using various algorithms. These algorithms may use coefficients, which may be empirically determined, and may correspond to the wavelengths of light used. The algorithms may be stored in a ROM 154 and accessed and operated according to processor 122 instructions. The monitor 102 may also include a detector/decoder 155 that may receive signals (via the receiver 128) from the encoder 120. The detector/decoder 155 may, for instance, decode the signals from the encoder 120 and may provide the decoded information to the processor 132. The decoded signals may provide information to the processor such as the type of the sensor 114 and the wavelengths of light emitted by the emitter 116 so that proper calibration coefficients and/or algorithms to be used for calculating the patient's 117 physiological characteristics may be selected and utilized by the processor 132.

The monitor 102 may also include a power source 156 that may be used to transmit power to the components located in the monitor 102. In one embodiment, the power source 156 may be one or more batteries, such as a rechargeable battery. The battery may be user-removable or may be secured within the housing of the monitor 102. Use of a battery may, for example, allow the oximeter 100 to be highly portable, thus allowing a user to carry and use the oximeter 100 in a variety of situations and locations. Additionally, the power source 156 may include AC power, such as provided by an electrical outlet, and the power source 156 may be connected to the AC power via a power adapter through a power cord (not shown). This power adapter may also be used to directly recharge one or more batteries of the power source 156 and/or to power the pulse oximeter 100. In this manner, the power adapter may operate as a charging device 158.

The sensor 114 may also include a charging control circuit 162, which may, for example, allow for the adaptive control of wireless energy harvested from the charging device 115 for use in the power source 160 of the sensor 114. In one embodiment, the power source 160 may be one or more batteries, such as a rechargeable battery that may be user-removable or may be secured within the housing of the sensor 114. Alternatively, the power source 160 may be one or more capacitors for storage of charge. The charging control circuit 162 may, for example, include a processing circuit that may determine the current level of charge remaining in the power source 160, as well as the current amount of power being harvested by the charging device. For example, the charging control circuit 162 may determine if the charging device 115 is generating too little power to charge the power source 160. In response to determining that the charging device 115 is generating too little power to charge the power source 160 and that the power source 160 is low on power, the charging control circuit 162 may generate an error signal that may be transmitted to the monitor 102 for generation of a corresponding error message for display on the display 104 of the monitor 102 by, for example, the processor 132. The error message may indicate to a user that the sensor 102 is low on power and may also direct the user to take action, such as changing the power source 160 (i.e., installing new batteries), charging the power source 160 (i.e. by plugging the sensor 102 into a charging unit or into an electrical outlet via a power adapter). Alternatively, the error message may indicate to a user that the recharging system of the sensor is potentially malfunctioning, and may direct the user, for example, to replace the sensor 114. In one embodiment, the error message may be generated when the charging control circuit 162 determines that the power source 160 has reached a certain charge level, for example 20% of the total charge remains in the power source 160. Additionally, as described below in greater detail, the charging control circuit 162 may also include conversion translation circuitry, such as a rectifier circuit, for conversion of alternating current generated via the charging device 115 into direct current.

Figure 3:
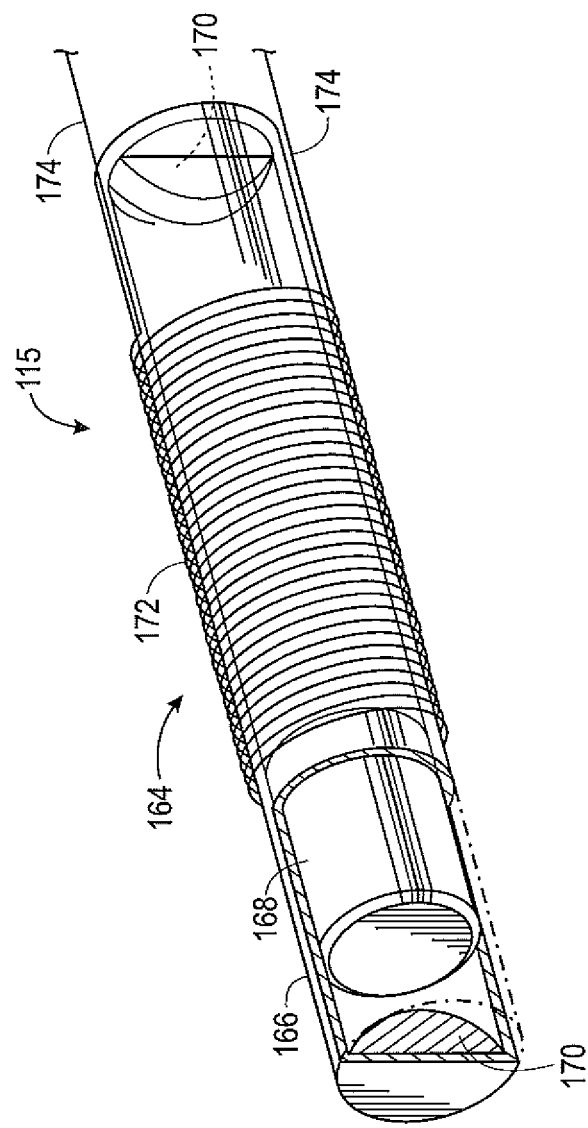
FIG. 3 illustrates the charging device of FIG. 1, in accordance with an embodiment.

Furthermore, the charging device 115 may be one of a multitude of energy harvesting components that utilize, for example, inductive energy generation techniques and/or piezoelectric energy generation techniques. Through use of these techniques, power may be harvested, for example, through motion of a patient 117, and utilized to directly recharge one or more batteries (or capacitors) of the power source 160 and/or to power the sensor 114. FIG. 3 illustrates a first embodiment of a charging device 115.

The charging device 115 may include an energy harvester 164 that includes a case 166, a magnet 168, one or more buffers 170, a coil 172, and one or more leads 174. It should be noted that one or more energy harvesters 164 may be utilized in conjunction with one another and that the energy harvester 164 may be sized to be imbedded in the sensor 114 or attached thereto. For example, the energy harvester 164, as well as the components that make up the energy harvester 164, may be, for example, microelectromechanical systems (MEMS) and/or nano electromechanical systems (NEMS) made up of components sized between 1 to 100 micrometers. However, the energy harvester 164, as well as the components that make up the energy harvester 164, may also be larger than MEMS and NEMS, as long as they may be integrated into or attached to a given sensor 114.

Returning to the components of the energy harvester 164, the case 166 may be composed of plastic or any other non-conducting material. The case 166 may enclose the magnet 168 and the buffers 170. The case 166 may also be sized to allow lateral movement of magnet 168. In one embodiment, the case 166 is cylindrical in shape. The magnet 168 may be sized to fit within the case 166 and move laterally within the case 166. The magnet 168 may be a permanent magnet. The magnet 168 may be capable of sliding from one end of the case 166 to the other in response to an input of kinetic energy. In one embodiment, the kinetic energy may include patient 117 movement that causes the magnet 168 to move through the case 166 of the energy harvester 164. The movement of the magnet 168 through the case 166 causes the magnet to pass through the coil 172. The coil 172 may be made up of a conductive substance and may be wrapped around the case 166. In one embodiment, the coil 172 may be made from coiled aluminum. In another embodiment, the coil 172 may be made from coiled copper wire. The copper wire may be covered by thin insulation.

As the magnet 168 passes through the coil 172, electricity is generated via electromagnetic induction. This electricity may then be transmitted via the leads 174 to the charging control circuit 162 or directly to the power source 160. In one embodiment, the generated electricity may be passed through a rectifier circuit, which may be located in, for example, the charging control circuit 162, and may translate the alternating current generated via electromechanical induction into direct current. The rectifier circuit may, for example, be a full wave rectifier made up of, for example, diodes. The rectification of the electricity by the rectifier circuit may also include smoothing the output of the rectifier circuit. A filter, such as a reservoir capacitor, may be used to smooth the output of the rectifier circuit prior to its transmission to the power storage device 160. Additionally, it should be noted that the leads 174 may include a single wire, two wires, or three wires (or other conductors) for allowing the leads 174 to conduct one, two, or three phase power.

The magnet 168 also may contact buffers 170 as it passes through the case 166. The buffers 170 may be made of elastic material such as rubber. In another embodiment, the buffers 170 may be springs. The buffers 170 at to help conserve the kinetic energy being focused into the sliding magnet 168 by redirecting the magnet 168 back through the case 166 when the buffer 170 is contacted by the magnet 168. In this manner, the buffers 170 aid in the conversion of kinetic energy into usable electricity.

Figure 4:
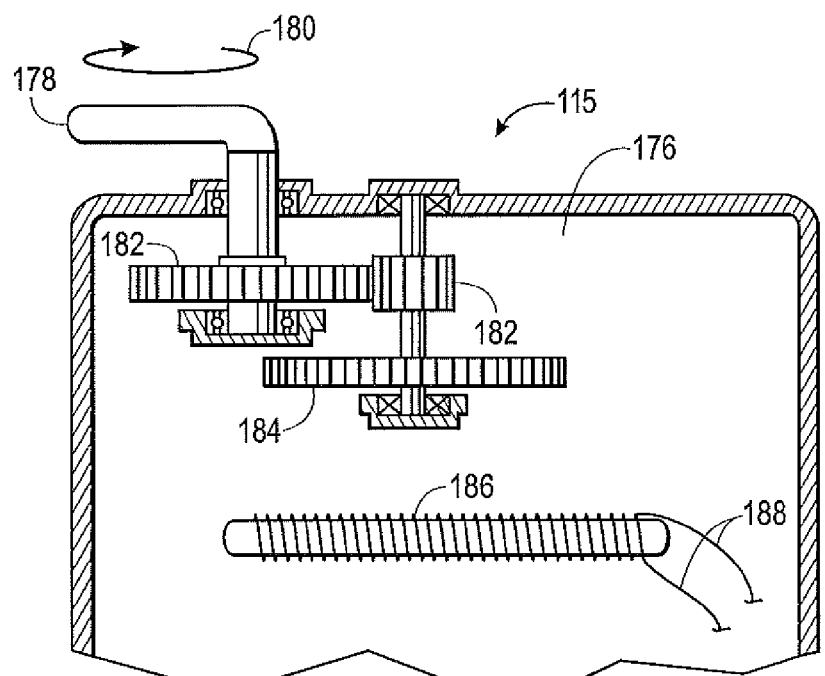
FIG. 4 illustrates the charging device of FIG. 1, in accordance with a second embodiment.

Another embodiment for the charging device 115 is illustrated in FIG. 4. The charging device 115 may include an energy harvester 176 that includes a mass 178 that may be utilized to generate rotational torque. One or more energy harvesters 176 may be utilized in conjunction with one another and the energy harvester 176 may be sized to be imbedded in the sensor 114 or attached thereto as MEMS, NEMS, or as other systems.

In operation, the mass 178 in energy harvester 176 may be free to rotate circumferentially 180 in response to movements by the patient 117. The mass 178 may be attached to a gear train 182. As the mass 178 rotates circumferentially 180, the gear train 182 may operate to transfer the rotational torque from the mass 178 to a permanent magnet 184, causing circumferential 180 rotation of the magnet 184. In one embodiment, the gear train 182 is set to create increased rotations of the magnet 184 relative to rotations of the mass 178. The magnet 184 may be positioned adjacent to a coil 186. The rotational motion of the magnet 184 induces an electrical current in the coil 186 which may be transmitted via conductive leads 188 to the charging control circuit 162 or directly to the power source 160. As noted above, the current generated may pass through a rectifier circuit, a transformer, or a phase converter as, for example, part of the charging control circuit 162. Accordingly, the energy harvester 176 may convert inputted kinetic energy, for example, movement by a patient 117 causing rotational movement of a mass 178, into electricity useable by the pulse oximeter 100.

Figure 5:
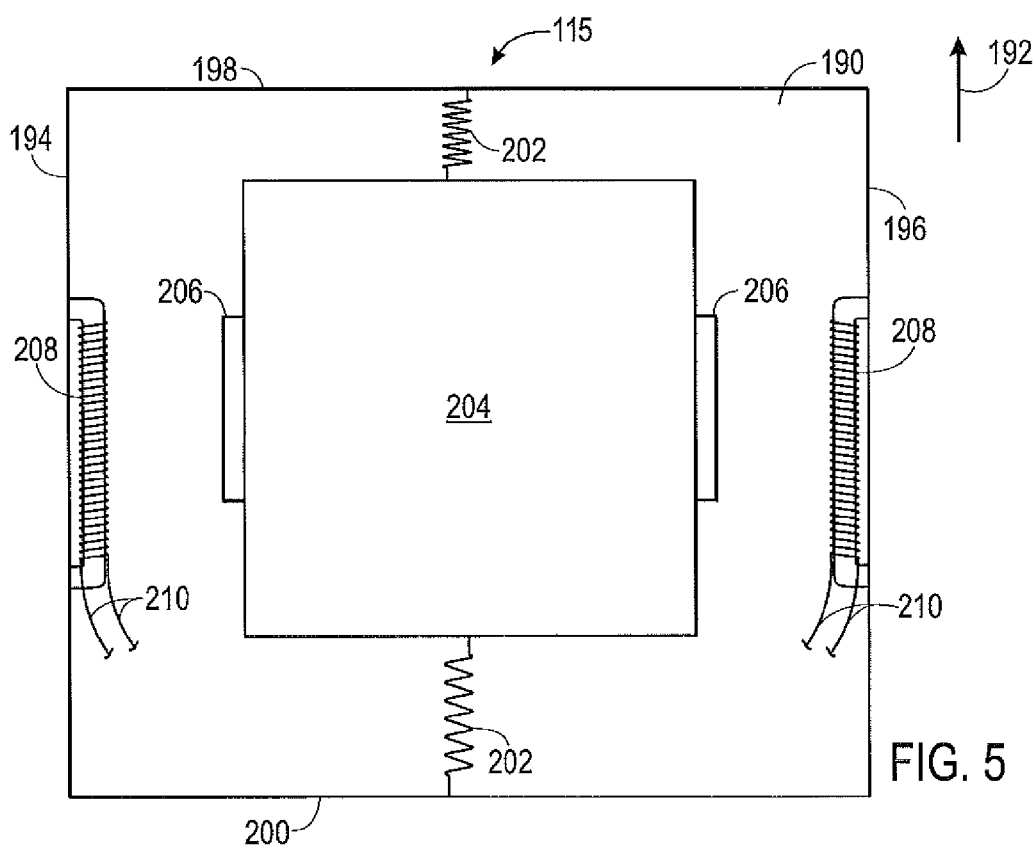
FIG. 5 illustrates the charging device of FIG. 1, in accordance with a third embodiment.

An additional embodiment for the charging device 115 is illustrated in FIG. 5. The charging device 115 may include an energy harvester 190 that may convert vibratory motion along an axis 192 into electrical energy. One or more energy harvesters 190 may be utilized in conjunction with one another and the energy harvester 190 may be sized to be imbedded in the sensor 114 or attached thereto as MEMS, NEMS, or as other systems. The energy harvester 190 may be enclosed by, for example, four partitions 194, 196, 198, and 200. As may be seen, partitions 194 and 196 may be opposite paired partitions while partitions 198 and 200 may also be opposite paired partitions. The energy harvester 190 may further include one or more attachment devices, such as springs 202, which may be utilized to suspend enclosure 204 from partitions 198 and 200. The springs 202 may allow for reciprocating movement of the enclosure 204 relative to partitions 194 and 196 only along the axis 192. This movement of the enclosure 204 may be in response to movement by the patient 117.

Additionally, the enclosure 204 of the energy harvester 190 may include one or more magnets 206 attached thereto. Accordingly, the enclosure 204, may allow for reciprocating movement of the magnets 206 relative to the partitions 194 and 196. Indeed, one or more coils 208 may be attached to the partitions 194 and 196 such that the reciprocating movement of the magnets 206 inductively generates a current in the coils 208. This induces current in coils 208 may be transmitted via conductive leads 210 to the charging control circuit 162 or directly to the power source 160. As noted above, the current generated may pass through a rectifier circuit, a transformer, or a phase converter as, for example, part of the charging control circuit 162. Accordingly, the energy harvester 190 may convert inputted kinetic energy, for example, movement by a patient 117 causing reciprocating movement of an enclosure 204 (and thus the magnets 206 attached thereto), into electricity useable by the pulse oximeter 100.

Figure 6A:
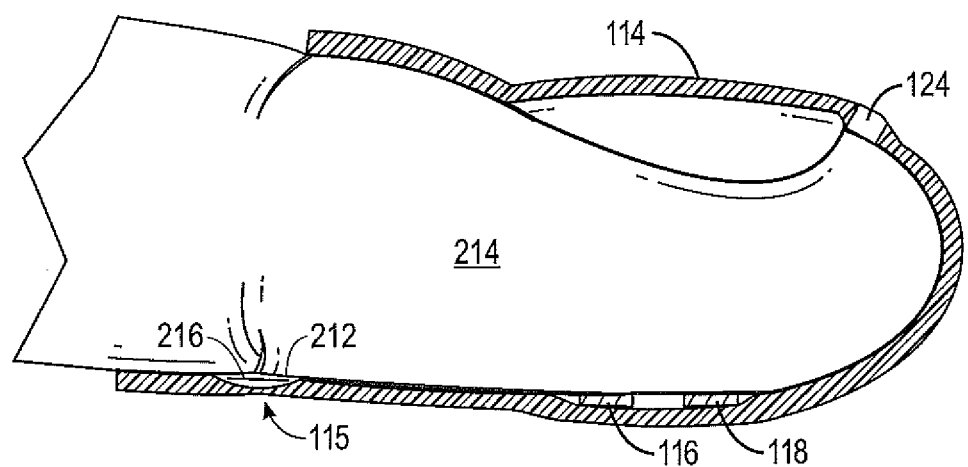
FIG. 6A illustrates the charging device of FIG. 1 in a first position, in accordance with a fourth embodiment.
Figure 6B:
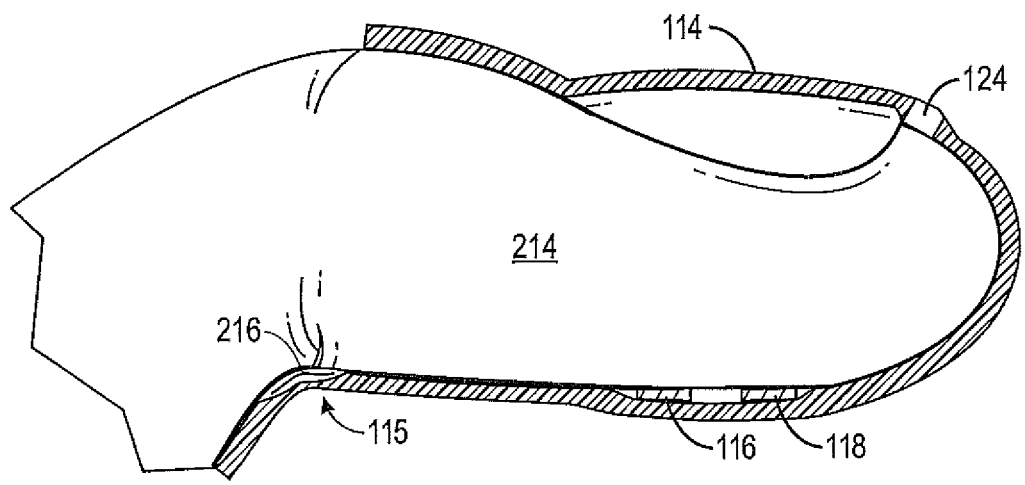
FIG. 6B illustrates the charging device of FIG. 1 in a second position, in accordance with a fourth embodiment.

FIGS. 6A and 6B illustrate an embodiment of the charging device 115 that makes use of a piezoelectric energy harvester 212 in a first and a second position, respectively. One or more piezoelectric energy harvesters 212 may be utilized in conjunction with one another and the piezoelectric energy harvester 212 may be sized to be imbedded in the sensor 114 or attached thereto as MEMS, NEMS, or as other systems.

FIGS. 6A and 6B illustrate a sensor 114 that may be utilized in conjunction with a finger 214 of a patient 117. As may be seen, the emitter 116 and the detector 118, as well as the transceiver 124 are illustrated as elements of the sensor 114. As depicted, the emitter 116 and detector 118 may be arranged in a reflectance-type configuration in which the emitter 116 and detector 118 are typically placed on the same side of the sensor site. Reflectance type sensors may operate by emitting light into the tissue (e.g., finger 214) and detecting the reflected light that is transmitted and scattered by the tissue. That is, reflectance type sensors detect light photons that are scattered back to the detector 118. The sensor 114 may alternatively be configured as a transmittance type sensor whereby the emitter 116 and detector 118 are typically placed on differing sides of the sensor site. In this manner, the detector 118 may detect light that has passed through one side of a tissue site to an opposite side of the tissue site.

As illustrated in both FIGS. 6A and 6B, the sensor 114 may also include a piezoelectric energy harvester 212. The piezoelectric energy harvester 212 may, for example, include a piezoelectric wire 216 contacted at two ends by conductive materials, such as metal, and mounted on a flexible substrate. This piezoelectric wire 216 may be comprised of, for example, Zinc Oxide (ZnO), Arium titanate (BaTiO$_3$), Lead titanate (PbTiO$_3$), Lead zirconate titanate (commonly known as PZT), and/or potassium niobate (KNbO$_3$). The piezoelectric wire 216 (as well as any piezoelectric material) has the ability to generate an electric potential in response to applied mechanical stress. Accordingly, piezoelectric wire 216 in the piezoelectric energy harvester 212 may operate to drive a current back and forth across the piezoelectric energy harvester 212 as the piezoelectric wire 216 is stretched, as may be seen in FIG. 6A, and compressed, as may be seen in FIG. 6B. This current may be transmitted to the charging control circuit 162 or directly to the power source 160 of the sensor 114. As noted above, the current generated may pass through a rectifier circuit, a transformer, or a phase converter as, for example, part of the charging control circuit 162. Accordingly, the piezoelectric energy harvester 212 may convert inputted kinetic energy, for example, movement by a patient 117 such as bending of a finger 214, into electricity useable by the pulse oximeter 100 via the piezoelectric wire 216.

Figure 7:
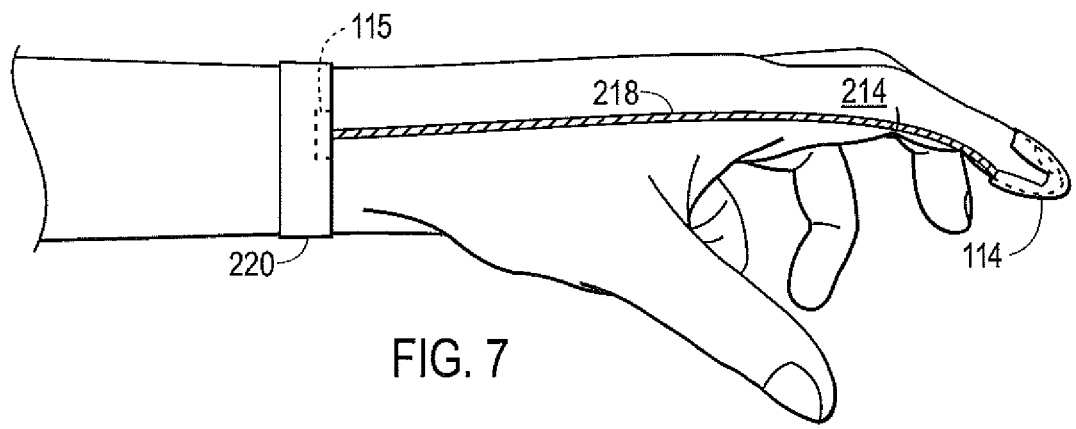
FIG. 7 illustrates the sensor and the charging device of FIG. 1, in accordance with a fifth embodiment.

FIG. 7 illustrates an embodiment whereby the charging device 115 may be located externally from the sensor 114. As illustrated, the charging device 115 may be attached to the sensor 114 via a lead 218. The lead 218 may be an electrical conductor, such as a power cable, that transmits harvested power to the sensor 114. The lead 218 may terminate with the charging device 115 which may be integrated into (or be attached to) a bracelet 220. The bracelet 220 may be, for example, a medical bracelet. Furthermore, the lead 218 may be connected to and separated from the charging device 115. That is, the lead 218 may be separable (i.e., releasable) from the charging device 115, the bracelet 220, and/or the sensor 114. Alternatively, the lead 218 may be permanently affixed to the charging device 115 and/or the bracelet 220. Regardless, by separating the charging device 115 from the sensor 114, more available area in the bracelet 220 may be available for harvesting of energy via patient 117 movement. That is, with greater area available for the charging device 115, a greater number of energy harvesters 164, 176, 190, and/or 212 may be utilized, thus increasing the overall amount of energy that may be harvested.

Figure 8:
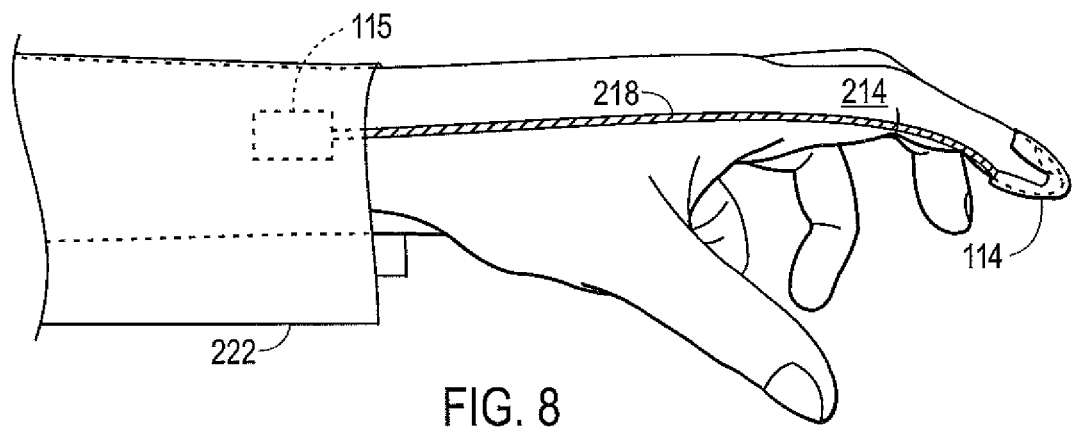
FIG. 8 illustrates the sensor and the charging device of FIG. 1, in accordance with a sixth embodiment.

FIG. 8 illustrates a second embodiment whereby the charging device 115 may be located externally from the sensor 114. As illustrated, the charging device 115 may be attached to the sensor 114 via a lead 218. The lead 218 may be an electrical conductor, such as a power cable, that transmits power to the sensor 114 and may terminate with the charging device 115 which may be integrated into (or be attached to) a garment 222. Again, the lead 218 may be separable (i.e., releasable) from the charging device 115, the garment 222, and/or the sensor 114. The garment 222 may be, for example, a shirt or a sleeve of a shirt. The use of the a garment 222 to house the charging device 115 may allow for the charging device 115 to be expanded in size, or for more than one charging devices 115 to be utilized in conjunction, while still allowing for the garment 222 to be comfortably worn. Thus a greater number of energy harvesters 164, 176, 190, and/or 212 may be utilized, which may increase the overall amount of energy that may be harvested. Additionally, by utilizing a large area, such as the garment 222, movements of a patient 117 across a plurality of regions of the patient 117 may be utilized to harvest energy from. That is, movements in the chest, arms, etc. of the patient 117 may be translated into power for use by the sensor 114. In this manner, a greater number of movements of a patient 117 may be harvested into power for use with the sensor 114 relative to energy harvesters 164, 176, 190, and/or 212 located in the sensor 114.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims.

What is claimed is:

1. A physiological sensor, comprising:
one or more motion sensitive structures disposed in a first housing of the physiological sensor and configured to generate power when moved, wherein the physiological sensor comprises a pulse oximetry sensor;
one or more sensing components which, acting alone or in combination, are capable of generating data related to one or more physiological parameters, wherein the one or more sensing components are disposed in a second housing of the physiological sensor, and wherein the second housing is separate from the first housing and configured to be placed adjacent to an external portion of tissue of a patient;
a memory element configured to store information specific to the physiological sensor; and
wireless communication circuitry capable of wirelessly transmitting the data related to the one or more physiological parameters;
wherein at least one of the one or more sensing components or the wireless communication circuitry are at least partially powered, directly or indirectly, by the one or more motion sensitive structures, wherein the information includes information regarding the one or more motion sensitive structures.

2. The physiological sensor of claim 1, comprising an energy storing structure that is at least partially charged by the one or more motion sensitive structures, wherein the one or more sensing components are at least partially powered by the energy storing structure.

3. The physiological sensor of claim 2, wherein the energy storing structure comprises a chargeable battery or a capacitor.

4. The physiological sensor of claim 1, wherein the one or more motion sensitive structures comprise an inductive energy harvester.

5. The physiological sensor of claim 1, wherein the one or more motion sensitive structures comprise a piezoelectric energy harvester.

6. A method for powering a wireless optical sensor, comprising the acts of:
generating power in a motion sensitive energy harvesting device disposed in a first housing of the wireless optical sensor in response to motion of a patient, wherein the wireless optical sensor comprises a pulse oximetry sensor, and wherein the wireless optical sensor comprises a memory element configured to store information specific to the wireless optical sensor, wherein the information includes information regarding the motion sensitive energy harvesting device; and
providing the power to one or more sensing components disposed in a second housing of the wireless optical sensor on the patient, wherein the second housing is separate from the first housing.

7. The method of claim 6, wherein the power is stored in a battery or capacitor prior to being provided to the one or more sensing components of the wireless optical sensor.

8. The method of claim 6, comprising utilizing the power by the wireless optical sensor to generate data related to one or more physiological parameters of the patient.

9. A monitoring system, comprising:
a wireless pulse oximetry sensor, comprising:
a light generating component;
a light detecting component capable of detecting light generated by the light generating component;
a wireless transmitter capable of wirelessly transmitting a signal based on the light detected by the light detecting component;
a power generating component that generates power in response to motion of the power generating component, wherein the generated power is provided to one or more of the light generating component, the light detecting component, or the wireless transmitter;
a charging control circuit configured to determine whether a level of charge generated by the power generating component is sufficient to charge an energy storage component of the wireless pulse oximetry sensor and to generate an error signal in response to determining that the level of charge is insufficient to charge the energy storage component; and a memory element configured to store information specific to the wireless pulse oximetry sensor, wherein the information includes information regarding the power generating component.

10. The monitoring system of claim 9, wherein the power generating component is incorporated into the wireless pulse oximetry sensor.

11. The monitoring system of claim 10, wherein the power generating component is separate from, but in communication with, the wireless pulse oximetry sensor.

12. The monitoring system of claim 10, comprising the energy storage component capable of storing the generated power prior to the power being provided to one or more of the light generating component, the light detecting component, or the wireless transmitter.

13. The monitoring system of claim 10, wherein the power generating component comprises a plurality of energy harvesting devices.

14. The monitoring system of claim 10, wherein the plurality of energy harvesting devices comprise inductive energy harvesting devices or piezoelectric energy harvesting devices.

15. The physiological sensor of claim 1, wherein the physiological sensor is configured to be disposed about a digit of the patient.

16. The physiological sensor of claim 1, comprising a charging control circuit configured to determine a level of charge generated by the one or more motion sensitive structures and to generate an error signal in response to determining that the level of charge is below a threshold charge level.

17. The physiological sensor of claim 16, wherein the wireless communication circuitry is configured to transmit the error signal to a patient monitor.

18. The method of claim 6, wherein the motion sensitive energy harvesting device comprises an inductive energy harvester or a piezoelectric energy harvester.

19. The method of claim 8, comprising transmitting, via a wireless transmitter disposed in the second housing of the wireless optical sensor, the data related to the one or more physiological parameters of the patient to a patient monitor.

20. The monitoring system of claim 10, wherein the wireless transmitter is configured to wirelessly transmit the error signal.

21. The monitoring system of claim 10, comprising a monitor configured to receive the error signal and to display an error message on a display based at least in part on the received error signal.

22. The monitoring system of claim 11, wherein the power generating component is disposed in a bracelet or a garment worn by the patient.

* * * * *